United States Patent
Kitagawa et al.

(10) Patent No.: US 9,586,196 B2
(45) Date of Patent: Mar. 7, 2017

(54) METAL NANOPARTICLE-PCP COMPLEX AND MANUFACTURING METHOD THEREFOR

(75) Inventors: Hiroshi Kitagawa, Kyoto (JP); Hirokazu Kobayashi, Kyoto (JP)

(73) Assignee: Kyoto University, Kyoto (JP)

( * ) Notice: Subject to any disclaimer, the term of this patent is extended or adjusted under 35 U.S.C. 154(b) by 37 days.

(21) Appl. No.: 14/237,292

(22) PCT Filed: Aug. 3, 2012

(86) PCT No.: PCT/JP2012/069845
§ 371 (c)(1),
(2), (4) Date: Feb. 5, 2014

(87) PCT Pub. No.: WO2013/021944
PCT Pub. Date: Feb. 14, 2013

(65) Prior Publication Data
US 2014/0186253 A1    Jul. 3, 2014

(30) Foreign Application Priority Data

Aug. 5, 2011  (JP) .................... 2011-171542

(51) Int. Cl.
*B01J 31/06* (2006.01)
*C01C 1/04* (2006.01)
(Continued)

(52) U.S. Cl.
CPC ............ *B01J 31/06* (2013.01); *B01J 23/40* (2013.01); *B01J 23/48* (2013.01); *B01J 23/70* (2013.01); *B01J 31/1691* (2013.01); *B01J 31/1815* (2013.01); *B01J 31/2239* (2013.01);

*B01J 35/0013* (2013.01); *B01J 35/0086* (2013.01); *C01C 1/0411* (2013.01); *C07C 51/00* (2013.01); *C07C 63/307* (2013.01); *C07C 65/03* (2013.01); *C08G 79/00* (2013.01); *C08K 3/00* (2013.01);
(Continued)

(58) Field of Classification Search
USPC ................. 423/362, 305; 556/130; 502/159; 428/402–402.24, 403, 404, 407, 321.1, 428/474.4; 427/331, 389.9, 212, 427/213–213.36, 483, 256
See application file for complete search history.

(56) References Cited

U.S. PATENT DOCUMENTS 9,139,601 B2 * 9/2015 Buso .................. C07F 3/003
2007/0219280 A1  9/2007 Kitagawa et al.
(Continued)

FOREIGN PATENT DOCUMENTS

JP    2005-075870 A    3/2005
JP    2005-255651 A    9/2005
(Continued)

OTHER PUBLICATIONS

Imaz et al., Angew. Chem. Int. Ed. 2009, 48, 2325-2329.*
(Continued)

*Primary Examiner* — Peter A Salamon
(74) *Attorney, Agent, or Firm* — Leydig, Voit & Mayer, Ltd.

(57) ABSTRACT

Provided is a composite, including a metal nanoparticle inside a porous coordination polymer (PCP), in which the PCP is formed of a metal ion and an organic ligand.

11 Claims, 5 Drawing Sheets

(51) Int. Cl.

| | |
|---|---|
| *C07C 65/03* | (2006.01) |
| *C08G 79/00* | (2006.01) |
| *C07C 63/307* | (2006.01) |
| *C08K 3/00* | (2006.01) |
| *C08L 85/00* | (2006.01) |
| *C07C 51/00* | (2006.01) |
| *B01J 31/16* | (2006.01) |
| *B01J 31/18* | (2006.01) |
| *B01J 31/22* | (2006.01) |
| *B01J 23/40* | (2006.01) |
| *B01J 23/48* | (2006.01) |
| *B01J 23/70* | (2006.01) |
| *B01J 35/00* | (2006.01) |
| *B82Y 30/00* | (2011.01) |
| *B82Y 40/00* | (2011.01) |
| *H01M 4/92* | (2006.01) |

(52) U.S. Cl.
CPC ........... *C08L 85/00* (2013.01); *B01J 2231/62* (2013.01); *B01J 2531/0213* (2013.01); *B01J 2531/26* (2013.01); *B01J 2540/10* (2013.01); *B82Y 30/00* (2013.01); *B82Y 40/00* (2013.01); *H01M 4/92* (2013.01)

(56) References Cited

U.S. PATENT DOCUMENTS

| | | |
|---|---|---|
| 2010/0174047 A1 | 7/2010 | Jung et al. |
| 2010/0183497 A1 | 7/2010 | Carpenter et al. |

FOREIGN PATENT DOCUMENTS

| | | |
|---|---|---|
| JP | 2006-248989 A | 9/2006 |
| JP | 2010-527890 A | 8/2010 |
| KR | 20080064077 A | 7/2008 |
| WO | WO 2008-143385 A1 | 11/2008 |

OTHER PUBLICATIONS

Hwang et al. Angew. Chem. Int. Ed. 2008, 47, 4144-4148.*
Cheon et al., *Angew Chem.*, 121(16): 2943-2947 (2009).
Gu et al., *J. Am. Chem. Soc.*, 133(31): 11822-11825 (2011).
Jiang et al., *Chem. Commu.*, 47(12): 3351-3370 (2011).
Liu et al., *Adv. Mater.*, 25(40): 5819-5825 (2013).
Müller et al., *Chem. Mater.*, 20(14): 4576-4587 (2008).
Rösler et al., *Eur. J. Inorg. Chem.*, 2014(32): 5514-5521 (2014).
Sugikawa et al., *Chem. Mater.*, 23(13): 3132-3134 (2011).
Tsuruoka et al., *ACS Appl. Mater. Interfaces*, 3(10): 3788-3791 (2011).
Zlotea et al., *J. Am. Chem. Soc.*, 132(9): 2991-2997 (2010).
European Patent Office, Extended European Search Report in European Patent Application No. 12821892.2 (Sep. 16, 2015).
Corma et al., *Chem. Rev.*, 110(8): 4606-4655 (2010).
El-Shall et al., *Journal of Materials Chemistry*, 19(41): 7625-7631 (2009).
Lohe et al., *Chem. Commun.*, 47: 3075-3077 (2011).
Meilikhov et al., *Eur. J. Onorg. Chem.*, 3701-3714 (2010).
Taniguchi et al., "Preparation of Pd Nano-particles Infiltrated into Elastic Metal Organic Frameworks and the Catalytic Properties," *Society of Nano Science and Technology Dai 10 Kai Taikai Koen Yokoshu, 10th*, item P2-50, p. 222 (Jun. 2012).
Turner et al., *Chem. Mater.*, 20(17): 5622-5627 (2008).
Japanese Patent Office, International Search Report in International Patent Application No. PCT/JP2012/069845 (Nov. 20, 2012).

* cited by examiner

FIG. 1

Fig. 2 a: COO⁻ Antisymmetric Stretch
b: COO⁻ Symmetric Stretch

METAL NANOPARTICLE-PCP COMPLEX AND MANUFACTURING METHOD THEREFOR

CROSS-REFERENCE TO RELATED APPLICATIONS

This patent application is the U.S. national phase of International Patent Application No. PCT/JP2012/069845, filed Aug. 3, 2012, which claims the benefit of Japanese Patent Application No. 2011-171542, filed on Aug. 5, 2011, which are incorporated by reference in their entireties herein.

TECHNICAL FIELD

The present invention relates to a composite complex including a metal nanoparticle and a porous coordination polymer (PCP), and a manufacturing method therefor.

BACKGROUND ART

It is essential to develop a PCP composite catalyst having a structure in which a nanocatalyst surface is covered by a PCP, in order to realize a highly efficient and highly selective reaction in which a gas involved in a catalytic reaction is trapped by the PCP and subjected to the reaction reliably.

In Non Patent Literature 1, after a PCP has been produced in advance, its formation of a composite with a metal nanoparticle is performed. Thus, the composite has a structure in which the metal nanoparticle adheres to the outside of the PCP, and exhibits a limited composite effect of the metal nanoparticle and the PCP.

In Non Patent Literature 2, a metal ion (Al or Cu) and a ligand (bpdc or btc) are caused to act in the presence of iron oxide to form a complex of the metal ion and the ligand. However, the complex is used for an application such as a sustained release formulation of a drug, iron oxide is used for transport of the complex to a target position with a magnet by means of its magnetism, an iron oxide nanoparticle merely integrates with a PCP on part of its surface, and an iron oxide particle is not present inside the PCP.

CITATION LIST

Non Patent Literature

[NPL 1] Eur. J. Inorg. Chem., 2010, 3701-3714
[NPL 2] ChemComm, 2011, 47, 3075-3077

SUMMARY OF INVENTION

Technical Problem

An object of the present invention is to provide a composite in which a metal nanoparticle interacts with a PCP.

Solution to Problem

The present invention provides the following composite and manufacturing method therefor.
Item 1. A composite, comprising a metal nanoparticle inside a porous coordination polymer (PCP), in which the PCP is formed of a metal ion and an organic ligand.
Item 2. The composite according to Item 1 or 2, wherein the metal nanoparticle comprises a noble metal nanoparticle.
Item 3. The composite according to item 1, wherein the composite has an average thickness of a PCP layer extending from a surface of the composite to the metal nanoparticle of 1 to 200 nm.
Item 4. The composite according to any one of items 1 to 3, wherein the PCP is formed of a metal ion, a ligand having a carboxyl group, and a nitrogen-containing aromatic compound that coordinates through a ring nitrogen atom.
Item 5. The composite according to any one of Items 1 to 4, wherein the metal nanoparticle comprises at least one kind of catalyst selected from the group consisting of gold, platinum, palladium, nickel, cobalt, manganese, chromium, silver, copper, iron, ruthenium, rhodium, zinc, and an alloy or oxide thereof.
Item 6. The composite according to any one of Items 1 to 5, wherein the composite has a size of 1 to 500 nm.
Item 7. The composite according to any one of Items 1 to 6, wherein 50% or more, 60% or more, 70% or more, 80% or more, 90% or more, or 95% or more of the metal nanoparticle are brought into contact with a gaseous reactant that passes through the PCP layer.
Item 8. A use of the composite according to any one of Items 1 to 7 as a catalyst.
Item 9. A manufacturing method for a compound, comprising subjecting the metal nanoparticle in the composite according to any one of Items 1 to 7 to a reaction with a gas to be adsorbed by the PCP to produce the compound.
Item 10. The manufacturing method according to Item 9, wherein the gas includes hydrogen and nitrogen, the metal nanoparticle comprises an iron-based catalyst, and the produced compound includes ammonia.
Item 11. The manufacturing method for a composite of any one of items 1 to 7, comprising mixing a metal ion with a polyvalent carboxylic acid ligand and/or a nitrogen-containing hetero ring ligand in the presence of a metal nanoparticle and a solvent.

Advantageous Effects of Invention

The PCP of the present invention is formed of a metal ion and an organic ligand coordinating thereto, and the diversity of substances obtained by combining the kinds of the metal ion and the organic ligand is almost infinite. As compared to an adsorbing material such as zeolite or activated carbon, the PCP has an extremely high degree of freedom in molecular design and has the property of an adsorbing material that stores a gas molecule in a large amount and stably. In addition, the PCP can take up a gas selectively and at a high concentration inside its pores. Thus, a porous coordination polymer (PCP) composite catalyst can serve as a catalyst material that is excellent in high efficiency and high selectivity surpassing the existing nanomaterial.

According to one embodiment of the present invention, there is provided a PCP composite particle of a core-shell type including a metal nanoparticie inside a PCP.

Further, a gas is selectively adsorbed by a PCP moiety so as to react with a metal catalyst, and hence a selective catalytic reaction becomes possible.

The PCP-based composite catalyst of the present invention can be widely applied and utilized to develop and research various catalysts by a purposeful and rational construction technique. In particular, the fixation of a homogeneous catalyst (molecular catalyst) to the PCP or the formation of a composite of the PCP with a nanometal catalyst can realize cost saving based on the long-term utilization of the homogeneous catalyst and a highly efficient and highly selective reaction involving "being taken up reliably (selective adsorption by the PCP) and subjected to a reaction reliably (substance conversion by a nanocatalyst)." in other words, only a by-product gas involved in catalytic activation can be trapped by the PCP and subjected to a reaction reliably. Further, in the PCP composite catalyst, in addition to the loading of a molecular catalyst or a nanocatalyst at a high density, a pore wall serves as the so-called "partition plate". Thus, sintering (degradation of active sites due to particle growth) can be prevented, and the aggregation and fusion of metal nanoparticles are suppressed. As a result, the lifetime of the metal nanocatalyst is expected to be lengthened. Further, a composite molecular catalyst as the homogeneous catalyst is fixed in the pores of the PCP. Accordingly, the catalyst can be prevented from flowing out and serves as a catalyst that may be used repeatedly.

In addition, the pores have an adsorbed gas, and hence poisoning with a gas serving as a catalyst poison can also be prevented. Meanwhile, there is a report that the nanopores of the PCP cause a molecular stress. Thus, it is expected that a substrate is deformed by a unique nanospace stress, resulting in its activation, and is further efficiently activated by the coexisting catalyst.

Hitherto, as the PCP composite catalyst, only one in which a catalyst is dispersed on the surface of a PCP has been obtained. Particularly when the catalyst is used for gas conversion, the ratio of an interface between the PCP and the catalyst is important. In this regard, the PCP has a micrometer-order size, i.e., is very large, its ratio of contact with an active metal species is very small, and hence it is very difficult to cause a highly efficient reaction.

The PCP composite of the present invention of a core-shell type in which a nanocatalyst is embedded inside a PCP or a nanocatalyst surface is covered by a PCP can cause a highly efficient reaction because its ratio of contact with an active metal species is very large.

DESCRIPTION OF EMBODIMENTS

Figure 4:
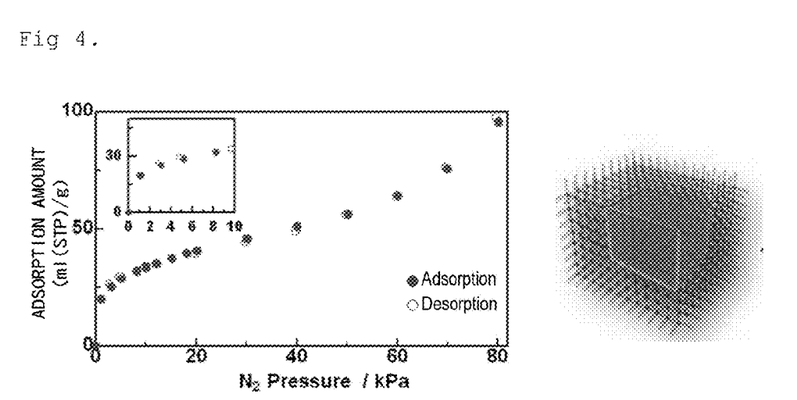
FIG. 4 is the $N_2$ adsorption isotherm (77 K) of a PCP-active metal species composite.

The composite of the present invention is a composite including a metal nanoparticle inside a porous coordination polymer (PCP). Herein, the phrase "including inside" means that: the metal nanoparticle is covered by the PCP; or the metal nanoparticle is embedded inside the PCP. As illustrated in, for example, the right side of FIG. 4, the PCP forms several layers to cover the entire metal nanoparticle. In the composite, only one metal nanoparticle is preferably present inside, but a plurality of metal nanoparticles may be present. The PCP has a number of pores. The pores are preferably formed in a three-dimensional manner as illustrated in FIG. 4, but may be formed in a two-dimensional or one-dimensional manner. In general, the pores of the PCP are regularly formed. The metal nanoparticle may be included inside while being fixed in close contact with the PCP, or may be included in a movable state inside the PCP. For example, inside the PCP having a bag form, at least one metal nanoparticle smaller than the inner cavity of the PCP may be included in a movable manner. A gaseous substance having affinity with the PCP passes through the pores to be concentrated and supplied to the surface of the metal nanoparticle inside, and the substance after the reaction is released out of the pores of the PCP. In order to perform a catalytic reaction using a metal nanoparticle catalyst, it is preferred that the PCP have high affinity with the gaseous substance as a reaction raw material and low affinity with the product after the reaction. As described above, a new substance is sequentially supplied from the PCP to the metal nanoparticle, and the product after the reaction is sequentially released out of the pores. Thus, when the metal nanoparticle is a catalyst, its reaction efficiency becomes very large. Examples of the metal nanoparticle catalyst include: a catalyst for manufacturing ammonia from hydrogen and nitrogen; a catalyst for producing hydrogen from ammonia, a hydrocarbon such as methane, ethane, or propane, or an alcohol such as methanol, ethanol, or propanol; and a catalyst for performing elongation with a group having 1 carbon atom, such as COOH, CHO, or $CH_2OH$, through a reaction with carbon dioxide, carbon monoxide, or the like.

For example, when the metal nanoparticle is a catalyst, a reaction substance necessary for a catalytic reaction can be concentrated on a catalyst surface, and a chemical reaction or the like can be efficiently performed. The size of the pores and the kind of a compound to be taken up in the pores can be changed freely by changing the kinds of a metal ion and ligand forming the PCP, and hence various reactions can be performed on the surface of the metal nanoparticle. By virtue of the presence of the PCP in the surface, even when the concentration of the gaseous substance as the reaction raw material outside the composite is low, the concentrations of the gaseous substance having affinity with the PCP inside the PCP and on the surface of the metal nanoparticle drastically increase. Thus, the presence of the PCP remarkably improves reaction efficiency. Further, the partial pressure of a gaseous reaction raw material in the case of performing the same reaction can be remarkably reduced.

In a preferred embodiment, the composite of the present invention has a core (metal nanoparticle)-shell (PCP) structure. In this case, in the composite having a core-shell structure, a single metal nanoparticle (core) may be covered by a PCP (shell), or a plurality of metal nanoparticles (cores) may be covered by a PCP (shell). Further, the composite of the present invention may be in a powder form, or may be in a film form such as a thin film form. In addition, the composite of the present invention, when in a powder form, may be formed into a particle form.

Figure 3:
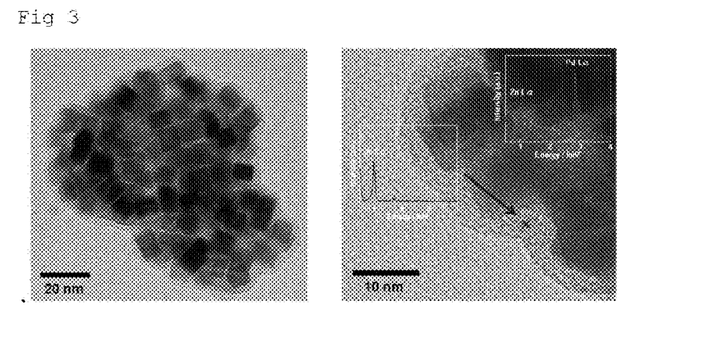
FIG. 3 are the TEM image (left) and EDS spectrum (right) of a PCP-active metal species composite.

The metal nanoparticle interacts (e.g., a chemical reaction or a catalytic reaction) with a gaseous substance supplied from the pores of the PCP. It is therefore preferred that the metal nanoparticle supply a surface capable of being utilized for a catalytic reaction or the like as much as possible inside the composite. Thus, the composite of the present invention suitably has a form such as a sheet form or a film form because a sufficiently large effective surface area is obtained even when a large number of metal nanoparticles are present. When the composite has a massive form, it is preferred that the particle size be small so that the number of metal nanoparticles confined inside becomes as small as possible. The composite in the case of having a massive form has a size of about 1 to 500 nm, preferably about 1 to 100 nm. When the particles are distributed in a lateral direction, the composite may include a number of particles. For example, the composite of FIG. 3 has a number of metal nanoparticles distributed in a lateral direction, and hence is a composite according to one preferred embodiment of the present invention. On the other hand, in the composite of FIG. 4, a number of reaction substances are supplied from the pores of the PCP to the metal nanoparticle, and the product after the reaction is released to the outside. A PCP layer needs to have a certain thickness in order to concentrate a gaseous substance, which is present outside, inside the PCP layer. However, when the thickness of the PCP layer is excessively large, it takes much time for the gaseous substance to reach the position at which the metal nanoparticle is present. The thickness of the PCP layer is preferably about 1 to 100 nm, more preferably about 1 to 20 nm.

Figure 5:
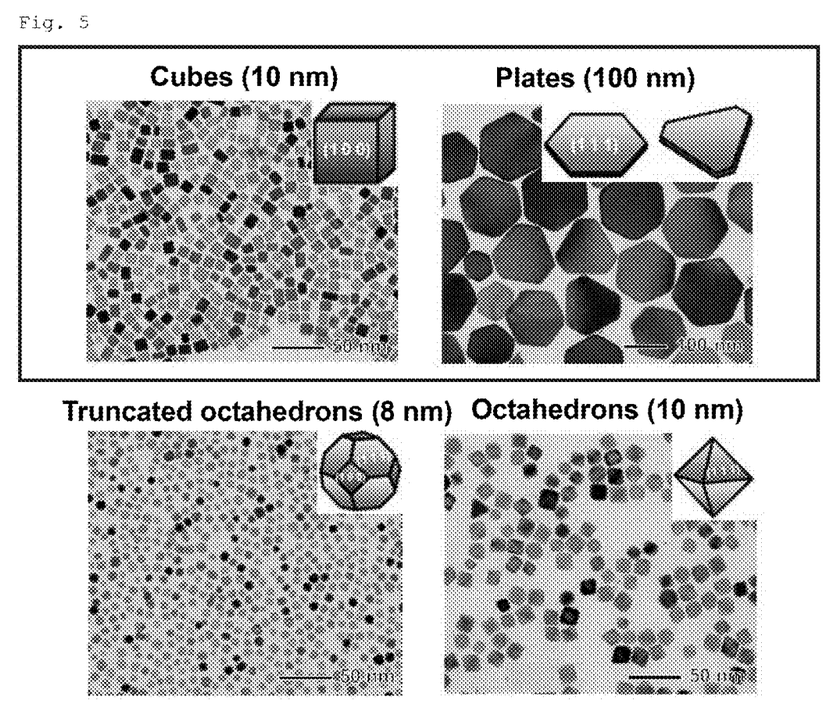
FIG. 5 show the forms (cubes, plates, truncated octahedrons, and octahedrons) of metal nanoparticles.

The metal nanoparticle of the present invention preferably has a form formed mainly of a plane, such as a cube, rectangular parallelepiped, plate, truncated octahedron, or (regular) octahedron form (FIG. 5), but may have any form such as a sphere, ellipsoid, or flake form.

The composite of the present invention has a structure in which the entire surface of the metal nanoparticle is covered by the PCP. A gaseous or liquid substance to be supplied from the outside is supplied to the surface of the metal nanoparticle through pores each having a predetermined size in the PCP. Thus, when the metal nanoparticle has a catalytic action, the composite of the present invention can provide a specific substance with high selectivity from a specific raw material (gas to be adsorbed by the PCP).

The metal nanoparticle is formed of a metal (including an alloy thereof) or a metal oxide.

Examples of the metal include gold, platinum, silver, copper, ruthenium, tin, palladium, rhodium, iridium, osmium, nickel, cobalt, zinc, iron, yttrium, magnesium, manganese, titanium, zirconium, and hafnium. Examples of the metal oxide include $PtO_2$, CuO, ruthenium(IV) oxide, rhodium oxide, ruthenium oxide, $Fe_2O_3$, $FeO_4$, ZnO, and osmium(IV) oxide.

The size of the metal nanoparticle is about 0.5 to 200 nm, preferably about 1 to 100 nm, more preferably about 5 to 20 nm.

The metal nanoparticle of the present invention may be subjected to surface treatment. Such surface treatment is preferably surface treatment with a hydrophilic polymer such as polyvinylpyrrolidone, polyacrylamide, polydimethylacrylamide, poly(meth)acrylate, polyoxyethylene oxide, polyoxyethylene alkyl ether, or polyvinyl alcohol. Such surface treatment allows the hydrophilic polymer to be bonded. Alternatively, a hydrophilic polymer having an SH group may be subjected to a reaction with the metal nanoparticle to introduce the hydrophilic polymer (surface treatment).

In another embodiment of the present invention, a compound having an SH group and any other reactive group (e.g., an amino group, a hydroxyl group, or a carboxyl group) is subjected to a reaction with the metal nanoparticle to produce a metal-S bond. The thus introduced other reactive group (e.g., an amino group, a hydroxyl group, or a carboxyl group) is subjected to a reaction with a ligand and a metal ion. Thus, a PCP layer can be formed. Alternatively, when a PCP constituent, i.e., a metal ion or an organic ligand can be caused to exist on the surface, or in the vicinity of the surface, of the metal nanoparticle through bonding, adsorption, an interaction, or the like, a PCP can be formed therefrom.

It should be noted that a bond between a polymer, compound, or the like having an SH group and the metal nanoparticle may be cleaved by photoirradiation. Thus, the surface of the metal nanoparticle may be exposed. This is because when the metal nanoparticle is used for a catalytic reaction or the like, it is desired to expose its active surface.

The composite of the present invention may be manufactured by: adding PCP constituents (a metal ion and a ligand) at low concentrations to a dilute solution (suspension) of a metal nanoparticle to form a PCP; and separating only a composite in which the metal ion is included inside the PCP by a technique such as centrifugation. According to such method, there is provided an advantage in that a catalytic reaction can be efficiently performed because the metal ion has not been subjected to surface treatment with a thiol compound or the like. The particle of the composite may also be made smaller to prevent the aggregation (overlapping) of the metal nanoparticles by performing the manufacture of the composite under the action of ultrasound or the like.

A substance for introducing a functional group capable of forming the PCP (capable of forming a coordination bond) into the surface of the metal nanoparticle is exemplified by p-mercaptophenol, aminobenzenethiol, p-mercaptopyridine, p-mercaptobenzoic acid, 11-mercapto-1-undecanol, and 11-mercaptoundecanoic acid. When the functional group capable of forming the PCP (capable of forming a coordination bond) is introduced into the metal nanoparticle via an SH group, the functional group is exemplified by one having a weaker bond to the metal nanoparticle than the SH group. When the metal nanoparticle is made of a metal oxide, the bonding to the metal nanoparticle can be achieved through an oxygen-containing functional group such as OH or COOH.

The metal nanoparticle to be used in the present invention may be manufactured in accordance with a known method. Specifically, the method may be exemplified by a method disclosed in Adv. Funct. Mater. 2009, 19, 189-200.

As the composite of the present invention, for example, for a Pd nanoparticle subjected to surface treatment used in Examples, a Pd nanocrystal having a cube form can be produced by performing reduction with addition of a reducing agent and a capping reagent for protecting only a (100) plane and controlling crystal growth to poly(N-vinyl-2-pyrrolidone) as a protective polymer and an aqueous solution of $Na_2PdCl_4$. The composite of the present invention may be obtained by constructing the PCP from the surface of the metal nanoparticle. It is desired to replace a metal surface by a self-assembled monolayer (SAM) having at its terminus the same functional group as that of a ligand component in the PCP. A metal nanoparticle-PCP composite may be produced by adding a PCP raw material to the metal nanoparticle replaced by the SAM, followed by heating and stirring.

The composite of the present invention may be manufactured in the same manner as above for a metal nanoparticle except for the Pd nanoparticle.

The PCP generally has two or more layers (e.g., 2 to 100 layers, preferably 3 to 50 layers, more preferably 4 to 30 layers, particularly 4 to 20 layers) formed of a metal and a ligand, and the layers are repeated. The PCP may be used for a solar cell element by, for example, changing the metal ion and/or the ligand for each layer to realize a series of flow of electrons.

Herein, the PCP is formed of a metal ion and an organic ligand, and may contain a counter anion. The metal ion is preferably an ion of, for example, magnesium, calcium, manganese, iron, ruthenium, cobalt, rhodium, nickel, palladium, copper, zinc, cadmium, titanium, vanadium, chromium, manganese, platinum, ruthenium, molybdenum, zirconium, or scandium, and is more preferably an ion of a metal such as magnesium, manganese, iron, cobalt, nickel, copper, or zinc. As the metal ion, a single metal ion may be used or two or more kinds of metal ions may be used in combination.

Examples of the ligand forming the PCP include: a compound in which two, three, or four carboxyl groups are bonded to an aromatic ring such as benzene, naphthalene, anthracene, phenanthrene, fluorene, indane, indene, pyrene, 1,4-dihydronaphthalene, tetralin, biphenylene, triphenylene, acenaphthylene, or acenaphthene (the ligand may be mono-, di-, or trisubstituted by a substituent such as: a halogen atom such as F, Cl, Br, or I; a nitro group; an amino group; an acylamino group such as an acetylamino group; a cyano group; a hydroxyl group; methylenedioxy; ethylenedioxy; a linear or branched alkoxy group having 1 to 4 carbon atoms such as methoxy or ethoxy; a linear or branched alkyl group having 1 to 4 carbon atoms such as methyl, ethyl, propyl, tert-butyl, or isobutyl; SH; a trifluoromethyl group; a sulfonic acid group; a carbamoyl group; an alkylamino group such as a methylamino group; or a dialkylamino group such as a dimethylamino group); an unsaturated divalent carboxylic acid such as fumaric acid, maleic acid, citraconic acid, or itaconic acid; and a nitrogen-containing aromatic compound (that may be mono-, di-, or trisubstituted by the substituent) capable of coordinating through two or more ring nitrogen atoms, such as pyrazine, 4,4'-bipyridyl, or diazapyrene. When the ligand is neutral, the PCP has a counter anion necessary for neutralizing the metal ion. Examples of such counter anion include a chloride ion, a bromide ion, an iodide ion, a sulfuric acid ion, a nitric acid ion, a phosphoric acid ion, a trifluoroacetic acid ion, a methanesulfonic acid ion, a toluenesulfonic acid ion, a benzenesulfonic acid ion, and a perchloric acid ion.

The PCP including a metal ion and an organic ligand encompasses a PCP having two-dimensional pores in a sheet form or the like or three-dimensional pores each including as a constituent a bidentate ligand in which a plurality of sheets coordinate to the axial position. Alternatively, for example, the following PCPs having one-dimensional pores may be used.

IRMOF-1, Zn4O(BDC)3 (H2BDC=benzenedicarboxylic acid)
MOF-69C, Zn3(OH2)(BDC)2
MOF-74, M2(DOBDC) (H2DOBDC=2,5-dihydroxyterephthalic acid, M=Zn, Co, Ni, Mg)
HKUST-1, Cu3(BTC)2 (H3BTC=1,3,5-benzenetricarboxylic acid)
MOF-508, Zn(BDC) (bipy)0.5
Zn-BDC-DABCO, Zn2(BDC)2(DABCO), (DABCO=1,4-diazabicyclo[2.2.2]-octane)
Cr-MIL-101, Cr3F(H2O)2O(BDC)3
Al-MIL-110, Al8(OH)12{(OH)3(H2O)3}[BTC]3,
Al-MIL-53, Al(OH)[BDC]
ZIF-8, Zn(MeIM)2, (H-MeIM=2-methylimidazole)
MIL-88B, Cr3OF(O2C—C6H4-CO2)3
MIL-88C, Fe3O(O2C—C10H6-CO2)3
MIL-88D, Cr3OF(O2C—C12H8-CO2)3
CID-1 [Zn2(ip)2(bpy)2] (Hip=isophthalic acid, bpy=4,4'-bipyridine)

The PCP to be used in the present invention is described in, for example, the following documents and reviews (Angew. Chem. Int. Ed. 2004, 43, 2334-2375; Angew. Chem. Int. Ed. 2008, 47, 2-14; Chem. Soc. Rev., 2008, 37, 191-214; PNAS, 2006, 103, 10186-10191; Chem. Rev., 2011, 111, 688-764; Nature, 2003, 423, 705-714.). However, the PCP is not limited thereto, and a known PCP or a PCP that may be manufactured in the future can be widely used.

The ratio between the PCP and the metal nanoparticle (weight ratio) is 1 to 99% by weight of the PCP: 99 to 1% by weight of the metal nanoparticle, preferably 10 to 50% by weight of the PCP: 50 to 90% by weight of the metal nanoparticle.

The following combinations are given as a combination of the gas to be adsorbed by the PCP (such as methane, ethane, carbon monoxide, carbon dioxide, ethylene, acetylene, benzene, or toluene), the metal nanoparticle catalyst (such as Au, Pt, Pd, or Ni), the other reaction component (such as hydrogen, ammonia, oxygen, water, silane, or HCN), and the product (such as formaldehyde, acetaldehyde, acetic acid, methanol, or ethanol). It should be noted that all the PCPs are applicable.

TABLE 1

| Absorbed substance (gas) | Nanometal catalyst | Other reaction component | Product |
|---|---|---|---|
| Nitrogen, hydrogen | Iron oxide, iron, ruthenium, ruthenium-silver | — | Ammonia |
| Methane, water | Nickel oxide | Carbon monoxide | Hydrogen |
| Methane, oxygen | Nickel oxide | Carbon monoxide, carbon dioxide | Hydrogen |
| Carbon monoxide, hydrogen | Nickel-based catalyst, ruthenium | — | Methane |
| Carbon monoxide, water | Iron oxide, chromium oxide, copper oxide, zinc oxide, nickel oxide | Carbon dioxide | Hydrogen |
| Carbon monoxide, oxygen | Platinum, palladium, gold, ruthenium | — | Carbon dioxide |
| Alcohol, oxygen | Gold, copper, platinum, palladium, ruthenium | — | Aldehyde, carboxylic acid |
| Carbon dioxide, hydrogen | Copper, copper-zinc oxide | — | Methanol |
| Methanol, oxygen | Gold, copper | — | Formaldehyde, formic acid |
| Styrene, hydrogen | Palladium, platinum | — | Ethylbenzene |
| Acetylene, hydrogen | Palladium, platinum, nickel, cobalt oxide | — | Ethylene |
| Aldehyde, hydrogen | Palladium, platinum, nickel | — | Alcohol |
| Ethylene | Silver, rhenium | — | Ethylene oxide |
| Nitrogen oxide, hydrogen | Palladium, platinum, silver, silver-rhodium, copper, nickel, iron oxide, manganese oxide, rhodium | — | Nitrogen, carbon dioxide, water |
| Oxygen, hydrogen | Platinum, palladium, platinum-ruthenium | — | Water |
| Propylene, hydrogen | Palladium, platinum | — | Propane |
| Butene, oxygen | Palladium, platinum | — | Butane |
| Ammonia | Ruthenium, palladium, platinum | — | Hydrogen, nitrogen |
| n-C6H14 water | Nickel, iron-copper | — | Methane, carbon monoxide, hydrogen, carbon dioxide |

TABLE 1-continued

| Absorbed substance (gas) | Nanometal catalyst | Other reaction component | Product |
|---|---|---|---|
| Nitro compound, hydrogen | Copper oxide, chromium oxide, nickel, cobalt oxide, zirconium oxide | — | Amine |

EXAMPLES

Hereinafter, the present invention is described in detail by way of Examples. It should be appreciated that the present invention is not limited to Examples below.

Example 1

Figure 1:
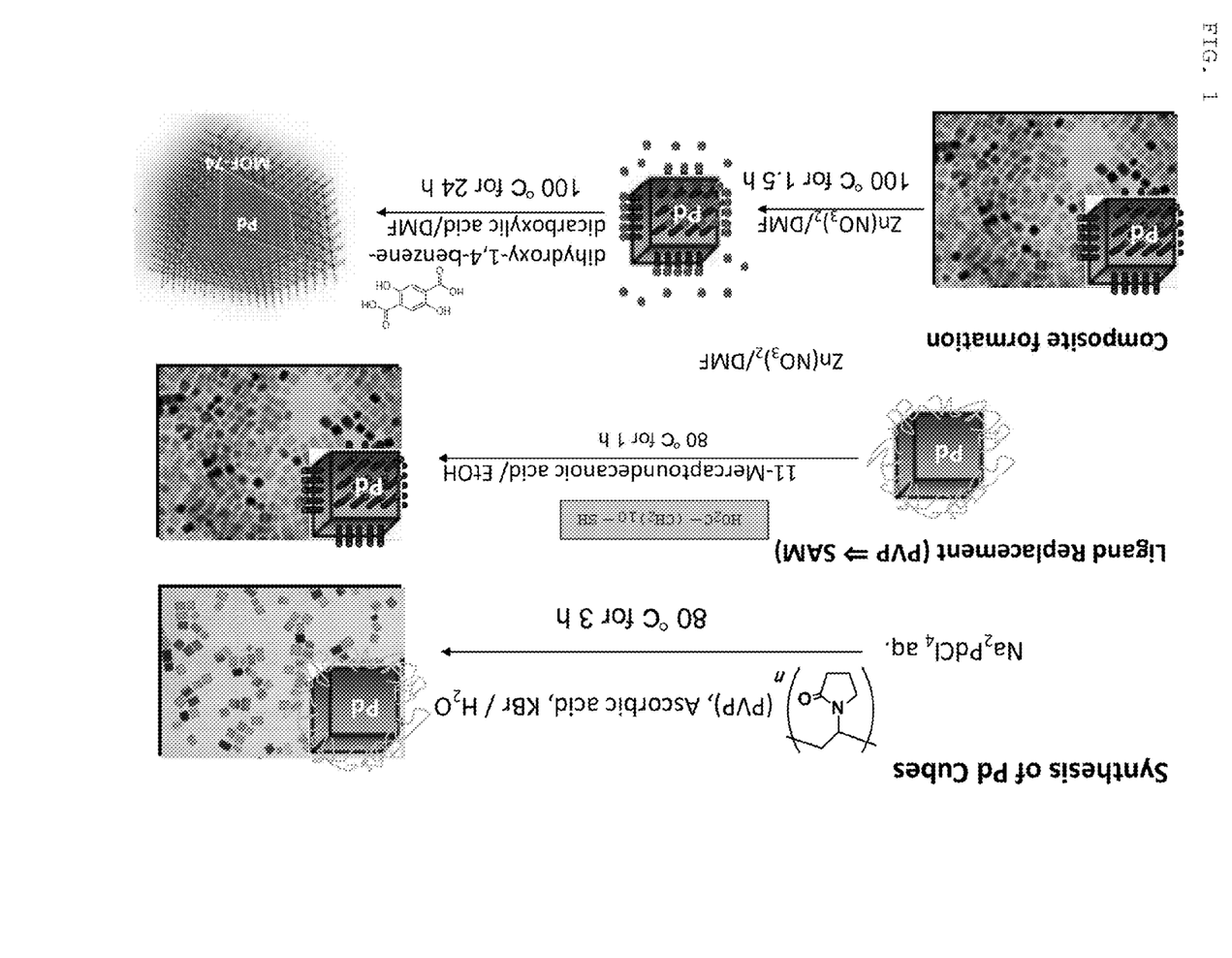
FIG. 1 is a scheme for synthesizing a PCP-active metal species composite.

(1) Synthesis of Pd Cubes (FIG. 1)

A cubic active metal species (Pd) was used to examine its formation of a composite with a PCP.

For the cubic Pd, polyvinylpyrrolidone (PVP; 105 mg), ascorbic acid (60 mg), and KBr (300 mg) were added to an aqueous solution (17.4 mM) of Na2PdCl4, and the mixture was reduced at 80° C. for 3 hours to yield a Pd nanoparticle (10 nm) in which PVP adhered to the surface.

(2) Ligand Replacement (PVP-SAM)

To the aqueous solution of the Pd nanoparticle obtained in (1) was added a solution of HOOC—$(CH_2)_{10}$—SH (70 mg) in ethanol, and the mixture was subjected to a reaction at 80° C. for 1 hour to bond HOOC—$(CH_2)_{10}$—SH to the Pd particle via an SH group.

HOOC—$(CH_2)_{10}$—SH was used for replacing a metal (Pd) surface by a self-assembled monolayer (SAM) having at its terminus the same functional group (COOH) as that of a ligand component in a PCP in order to construct the PCP from the surface of the active metal species.

(3) Composite Formation

Zn(NO3)2/DMF (40 mg) was added to the water suspension of the particle in which the metal (Pd) surface was replaced by the self-assembled monolayer (SAM), and the mixture was subjected to a reaction at 100° C. for 1.5 hours to bond a Zn ion to the terminal COOH group of HOOC—$(CH_2)_{10}$—SH. Then, a solution of dihydroxy-1,4-benzenedicarboxylic acid (10 mg) in DMF was added, and the mixture was heated and stirred at 100° C. for 24 hours to produce an active metal species-PCP composite (FIG. 1).

Figure 2:
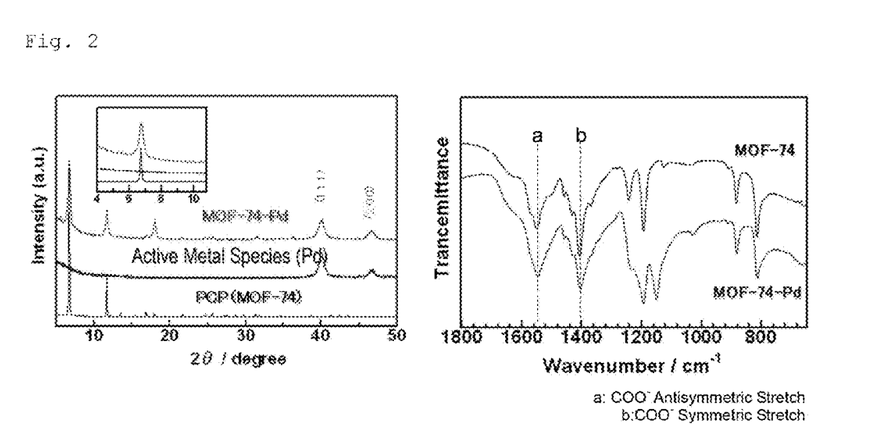
FIG. 2 are the XRD pattern (left) and IR spectrum (right) of a PCP-active metal species composite.

FIG. 2 show the results of powder X-ray diffraction of the resultant composite. In the powder X-ray diffraction pattern of the composite, diffraction peaks assigned to the active metal species and the PCP were each observed. Further, the results of infrared absorption spectrum measurement showed stretching vibrations assigned to the PCP at the same positions as those in a single PCP, confirming that a product of interest was obtained. It is understood that the XRD peaks of the PCP forming the composite are broad as compared to those of the PCP alone. The results indicate that the PCP in the produced PCP composite has a small crystallite size.

In view of the foregoing, in order to examine the composite state of the PCP and the active metal species, high-resolution TEM observation using a transmission electron microscope and EDS spectrum measurement were performed. It is understood from FIG. 3 that a very thin film was formed around the cubic active metal species. In order to investigate the components of the film, EDS spectrum analysis was performed. A spectrum assigned to the active metal species and a metal ion forming the PCP was obtained at a central portion. On the other hand, when a surface portion was analyzed, only a metal ion component forming the PCP was obtained. Thus, a composite in which the PCP film was formed around the active metal species was successfully obtained. Hitherto, there has been no report example of a core-shell type PCP composite in which a nanocatalyst surface is covered by a PCP, and hence this result is the first example.

In order to examine whether the resultant composite was actually a porous material, the measurement of the adsorption isotherm of nitrogen at 77 K was performed. FIG. 4 shows the results of the adsorption measurement. Adsorption caused by macropores on a low-pressure side was observed along with an N2 pressure, and hence this composite was found to be porous. As described above, a method involving covering the surroundings of the active metal species by the PCP was successfully found.

Example 2

Figure 6:
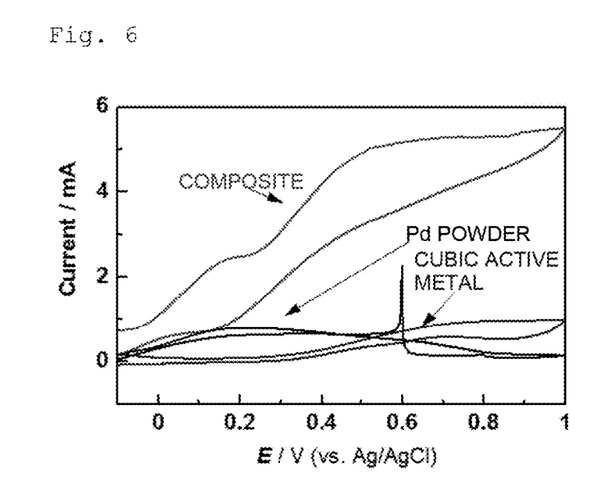
FIG. 6 is the cyclic voltammogram of Pd powder (black), a cubic active metal species (blue), and a compositex (red).

The composite obtained in Example 1 was used as an electrode catalyst to carry out a formic acid oxidation reaction. 2.5 mg of each of the cubic active metal species and the composite and 2.5 mg of a carbon paste (CPO) were added to a mixed solvent of 11.5 µl of ethanol and 11.5 µl of "Nafion (trademark)" (manufactured by Du Pont, a 10-fold diluted sample having a solid content concentration of 5 mass %), and the mixture was subjected to ultrasound irradiation to prepare a suspension. 23 µL of the suspension were applied onto a glassy carbon electrode (diameter: 3 mm, electrode area: 7.1 mm$^2$) and dried to produce a modified electrode. The modified electrode was soaked in a mixed solution of 0.5 M sulfuric acid and 1.0 M formic acid, and the potential was cycled at a scanning speed of 10 mV/s in a scanning range of −0.1 to 1.00 V with respect to a silver/silver chloride electrode potential at room temperature under an atmospheric pressure in an argon atmosphere. FIG. 6 shows the results.

As in Literature 1 (J. Phys. Chem. C 2010, 114, 21417-21422), current peaks corresponding to the formic acid oxidation reaction can be confirmed at around 0.15 V and 0.65 V in the case of using Pd powder. A catalytic current corresponding to the formic acid oxidation reaction was observed in the composite as well, and hence the composite was found to have a catalytic activity. In addition, the composite has a formic acid oxidation current value of about 2 mA, and exhibits a very high catalytic activity as compared to the current value of the cubic active metal species. Thus, the covering by the PCP was found to drastically improve the catalytic activity.

INDUSTRIAL APPLICABILITY

A technology involving loading the catalyst onto the PCP is also very important because the technology can also be widely applied and utilized to develop and research various catalysts ranging from a homogeneous catalyst to a non-homogeneous catalyst, which is directly used as a solid phase. Specifically, the technology can serve as a basic technology that has impacts on the industry in many fields such as ammonia synthesis and an organic reaction catalyst (e.g., a cross coupling reaction or a metathesis reaction). The composite is also useful as an electrode catalyst for a fuel cell using hydrogen, methanol, formic acid, or the like as fuel. When a PCP that can concentrate a substrate is used, it is expected that a reaction proceeds with high efficiency and a high current efficiency is exhibited. Further, in a system using methanol and formic acid, there is a problem in that carbon monoxide as an intermediate product serves as a catalyst poison to reduce the catalytic activity of an electrode. However, the use of a PCP that adsorbs carbon monoxide allows produced carbon monoxide to be adsorbed by the PCP and released out of the system, and hence the composite can serve as an electrode catalyst that allows a reaction to proceed efficiently and also has durability. The composite is also useful in a redox reaction on an electrode, and can cause a reaction at a potential having lower energy and efficiently by virtue of the substrate concentrating effect of the PCP, a molecular stress, and the like. When the composite is used as an electrode catalyst for reducing $CO_2$, $CO_2$ can be taken up at a high density inside the pores of the PCP to produce an oxygen-containing compound such as formic acid or oxalic acid through a reaction with electrons. Further, a product can be quickly removed out of the pores by making the inside of the pores of the PCP hydrophobic, and hence a deterioration in catalytic activity due to sintering (aggregation of particles) can be prevented. Further, in the case of the oxidation reaction of carbon monoxide as well, only carbon monoxide and oxygen can be concentrated and subjected to a reaction with an internal metal catalyst by synthesizing a PCP that can adsorb only CO and O2 (configured to have an open metal site or have a pore diameter that allows only CO and $O_2$ to pass). When a reaction essential for carbon-carbon bond formation (e.g., a cross coupling reaction or a metathesis reaction) is performed, the composite is designed so that only organic matter (substrate) having a certain size can be taken up by making the inside of the pores of the PCP hydrophobic and controlling the size of the pores, and can cause a selective reaction. Thus, the composite can also serve as a useful organic reaction catalyst having high selectivity under a mild condition. Further, the adsorption and reaction of, for example, only an olefin having a double bond can be achieved by providing an unsaturated site in the pores. Only a substrate of interest can be subjected to a reaction with high efficiency and high selectively by taking the pore diameter of the PCP, the properties (hydrophobicity and hydrophilicity) of the inside of the pores, and the unsaturated site into consideration as described above.

The invention claimed is:

1. A composite having a core-shell structure in which a core is covered by a shell,
    wherein the core comprises a metal nanoparticle, the shell comprises a porous coordination polymer (PCP), and the PCP is formed of a metal ion and an organic ligand,
    wherein the PCP forms layers that cover the metal nanoparticle,
    wherein the PCP has an average thickness extending from a surface of the composite to the metal nanoparticle of 1 to 200 nm,
    wherein the metal nanoparticle comprises a noble metal nanoparticle, and
    wherein the organic ligand forming the PCP is selected from the group consisting of
    (a) a compound in which two, three, or four carboxyl groups are bonded to an aromatic ring selected from the group consisting of benzene, naphthalene, anthracene, phenanthrene, fluorene, indane, indene, pyrene, 1,4-dihydronaphthalene, tetralin, biphenylene, triphenylene, acenaphthylene, and acenaphthene, wherein the ligand is optionally mono-, di-, or trisubstituted by a substituent selected from the group consisting of halogen atoms, a nitro group, an amino group, an acylamino group, a cyano group, a hydroxyl group, methylenedioxy, ethylenedioxy, a linear or branched alkoxy group having 1 to 4 carbon atoms, a linear or branched alkyl group having 1 to 4 carbon atoms, SH, a trifluoromethyl group, a sulfonic acid group, a carbamoyl group, an alkylamino group, and a dialkylamino group,
    (b) an unsaturated divalent carboxylic acid, and
    (c) a nitrogen-containing aromatic compound that coordinates through two or more ring nitrogen atoms, wherein the compound is optionally mono-, di-, or trisubstituted by the substituent.

2. A composite having a core-shell structure in which a core is covered by a shell,
    wherein the core comprises a metal nanoparticle, the shell comprises a porous coordination polymer (PCP), and the PCP is formed of a metal ion and an organic ligand,
    wherein the PCP forms layers that cover the metal nanoparticle,
    wherein the PCP has an average thickness extending from a surface of the composite to the metal nanoparticle of 1 to 200 nm,
    wherein the metal nanoparticle comprises at least one metal selected from the group consisting of gold, platinum, palladium, nickel, cobalt, manganese, chromium, silver, copper, iron, ruthenium, rhodium, zinc, and an alloy or oxide thereof, and
    wherein the organic ligand forming the PCP is selected from the group consisting of
    (a) a compound in which two, three, or four carboxyl groups are bonded to an aromatic ring selected from the group consisting of benzene, naphthalene, anthracene, phenanthrene, fluorene, indane, indene, pyrene, 1,4-dihydronaphthalene, tetralin, biphenylene, triphenylene, acenaphthylene, and acenaphthene, wherein the ligand is optionally mono-, di-, or trisubstituted by a substituent selected from the group consisting of halogen atoms, a nitro group, an amino group, an acylamino group, a cyano group, a hydroxyl group, methylenedioxy, ethylenedioxy, a linear or branched alkoxy group having 1 to 4 carbon atoms, a linear or branched alkyl group having 1 to 4 carbon atoms, SH, a trifluoromethyl group, a sulfonic acid group, a carbamoyl group, an alkylamino group, and a dialkylamino group,
    (b) an unsaturated divalent carboxylic acid, and
    (c) a nitrogen-containing aromatic compound that coordinates through two or more ring nitrogen atoms, wherein the compound is optionally mono-, di-, or trisubstituted by the substituent.

3. The composite according to claim 1, wherein the metal nanoparticle has a size of 1 to 200 nm.

4. The composite according to claim 1, wherein 50% or more of the metal nanoparticle is brought into contact with a gaseous reactant that passes through the PCP layer.

5. A method of producing a compound, comprising contacting the composite of claim 1 with a gaseous substance such that the metal nanoparticle in the composite is subjected to a reaction with the gaseous substance adsorbed by the PCP to produce the compound.

6. The method according to claim 5, wherein the gas substance comprises hydrogen and nitrogen, the metal nanoparticle comprises an iron-based catalyst, and the produced compound comprises ammonia.

7. The composite according to claim 2, wherein the metal nanoparticle has a size of 1 to 200 nm.

8. The composite according to claim 7, wherein 50% or more of the metal nanoparticle is brought into contact with a gaseous reactant that passes through the PCP layer.

9. The composite according to claim 1, wherein a carboxy group is introduced into the metal nanoparticle via an SH group.

10. A method of producing a compound, comprising contacting the composite of claim 2 with a gaseous substance such that the metal nanoparticle in the composite is subjected to a reaction with the gaseous substance absorbed by the PCP to produce the compound.

11. The method according to claim 10, wherein the gas substance comprises hydrogen and nitrogen, the metal nanoparticle comprises an iron-based catalyst, and the produced compound comprises ammonia.

* * * * *